United States Patent [19]
Hertz

[11] Patent Number: 5,813,857
[45] Date of Patent: Sep. 29, 1998

[54] TONGUE DEFLECTOR FOR USE WITH SALIVA EJECTORS

[76] Inventor: Reuben Hertz, 2318 Sea Island Dr., Ft. Lauderdale, Fla. 33301

[21] Appl. No.: 682,320

[22] Filed: Jul. 17, 1996

[51] Int. Cl.⁶ .................................................. A61C 17/10
[52] U.S. Cl. ............................ 433/93; 433/140; 600/238
[58] Field of Search .................... 433/91, 93, 94, 433/95, 96, 136, 140, 116; 600/195, 239, 240, 241, 237, 238; 128/848, 859, 860

[56] References Cited

U.S. PATENT DOCUMENTS

| | | | |
|---|---|---|---|
| 2,603,870 | 7/1952 | Nordin | 483/93 |
| 2,937,445 | 5/1960 | Erickson | 433/93 |
| 3,363,622 | 1/1968 | Mendola | 433/140 |
| 3,396,468 | 8/1968 | Dayhoff | 433/93 |
| 3,802,081 | 4/1974 | Rogers | 433/93 |
| 4,281,986 | 8/1981 | Erickson | 433/93 |
| 4,289,127 | 9/1981 | Nelson | 433/93 |

*Primary Examiner*—Cary E. O'Connor

[57] ABSTRACT

This invention relates to tongue deflectors which attach to saliva ejectors. The tongue deflector of this invention is formed of a flattened body with sufficient height to extend from the floor of the mouth to the top of tooth surfaces, so that the body may extend along the inner sides of the teeth to separate contact between the tongue and at least some of the teeth. A plurality of slotted cuts are provided through the body of the device to form a plurality of straps which may be pulled or pushed away from the body. The saliva ejector stem is passed through the strap so the saliva ejector tip nests in the tongue deflector body, and the tongue deflector attaches to the saliva ejector tip.

7 Claims, 6 Drawing Sheets

TONGUE DEFLECTOR FOR USE WITH SALIVA EJECTORS

FIELD OF THE INVENTION

This invention relates to saliva ejectors, tongue guards, and other intra-oral dental devices used to remove, drain or suction oral fluids. More particularly, this invention relates to tongue deflectors which attach to saliva ejectors.

DESCRIPTION OF PRIOR ART

The basic dental saliva ejector consists of a tube made of flexible plastic with one end connected to a source of vacuum and with the opposite end containing an aperture tip adapted for placement in a patient's mouth. Upon the application of vacuum, fluid is drawn into the saliva ejector through the aperture tip. Various saliva ejectors devices have been developed to provide various additional functions including jaw support, restriction of the lip, tongue and/or cheek. Such devices are bulky, expensive, difficult to assemble and disassemble, clean and sterilize, made of plastic or metal, and are non-disposable since the cost of manufacture is significantly more than the profit derived from a single procedure. Other dental devices have been developed as accessory equipment for conventional saliva ejectors. To date these implements have met with limited commercial success due to their inability to reliably prevent the soft tissue in the mouth from blocking the ejector tip or to protect the tongue against abrasion from dental instruments. According to U.S. Pat. No. 4,354,837 to Moore, issued Oct. 19, 1982, the tongue guard is designed to only fit a specific type of saliva ejector tip, requiring a specific saliva ejector diameter and grove opening for attachment. Also, it is only adjustable and lockable into position in the direction of the groves on the saliva ejector tip. In U.S. Pat. No. 4,017,975 to Johnson, issued Apr. 19, 1977, the saliva ejector and tongue deflector are integrated into a single functioning unit, where apertures in the body of the tongue deflector act as the saliva ejector. Due to the inflexible design of the Johnson apparatus, it is not usable for all procedures, and thus never commerciality accepted. The most widely used disposable saliva ejectors are of the type presented in U.S. Pat. No. 4,074,435 to Orsing, issued Feb. 21, 1978. These devices only perform the function of the saliva ejector, and comprise of a tubular stem formed of flexible material open at both ends thereof one end of which forms a suction inlet opening when the other end thereof is connected to a suction tube. A grooved sleeve on the other end of the tube is provided in order to avoid soft tissue drawing. The simplicity and disposability of Orsing's device has made it a standard in the dental industry.

Thus it is the objective of the present application to enhance the standard disposable saliva ejector of Orsing, by providing the added functionality of retracting the tongue or cheek within the oral cavity (mouth), so as to maintain clear channel for fluid flow to the ejector tip without interference by the soft tissue in the mouth. The tongue deflector of the present invention in inexpensive, disposable and readily adjustable into various fixed positions for assuring positive retraction of the tongue during any dental operatory procedures on mandibular teeth. The tongue deflector is attachable to the disposable saliva ejectors of various diameters in plurality of configurations while providing adjustments for the patient's mouth size and curvature of the mouth. Since it is fabricated of soft pliable and flexible material, it may be reshaped or reconfigured using ordinary instruments to best fit the individual mouth shape of patients. The tongue guard of the present invention works with saliva ejectors of various tip configurations.

SUMMARY OF THE INVENTION

It is, accordingly, the object of the present invention to provide a new and improved dental tongue deflector which easily connects to any standard saliva ejector and functions to assure positive retraction of the tongue and cheek during dental procedures, while not interfering with saliva ejector function.

It is further object of the present invention to provide a dental appliance for use in combination with saliva ejector which maintains a clear channel for fluid flow to the saliva ejector.

It is another object of the present invention to provide a dental appliance for use in combination with a saliva ejector which increases the visibility and access for the dentist for performing surgical and/or dental restorative procedures.

It is yet another object of the present invention to provide a dental appliance for use in combination with a saliva ejector which is readily mounted to the saliva ejector and can positioned in a plurality of adjustable positions.

It is another objective of the present invention to provide a dental appliance for use in combination with a saliva ejector which is inexpensive and readily expendable for disposable use.

It is another object of the present invention to provide a dental appliance for use in combination with a saliva ejector which is made of a single flexible component readily adjustable in size.

It is another object of the present invention to provide a dental appliance for use in combination with a saliva ejector which is reversible and can be used on both the left side or right side of the mouth.

It is another object of the present invention to provide a dental appliance for use in combination with a saliva ejector which slides onto a saliva ejector of various diameters and tip types.

It is another object of the present invention to provide a dental appliance for use in combination with a saliva ejector which provides sufficient separation between the tongue and the dental instruments, while will not damaging dental instruments when contact is made.

It is yet another objective of the present invention to provide a dental appliance for use in combination with a saliva ejector which readily conforms to the shape of the patient's mouth.

Additional objects and advantages of the invention will be set forth in part in the description which follows and in part will be obvious from the description, or may be learned by practice of the invention. The objects and advantages of the invention may be realized and attained by means of the instrumentalities and combination particularly pointed out in the appended claims.

To achieve the foregoing objects and in accordance with the purpose of the invention, as embodied and broadly described herein, the tongue deflector of this invention is formed of a flattened body with sufficient height to extend from the floor of the mouth to the top of tooth surfaces, so that the body may extend along the inner sides of the teeth to separate contact between the tongue and at least some of the teeth. A plurality of slotted cuts are provided through the body of the device to form a plurality of straps which may be pulled or pushed away from the body. The saliva ejector stem is passed through the strap so the saliva ejector tip nests in the tongue deflector body, and the tongue deflector attaches to the saliva ejector tip.

DESCRIPTION OF THE PREFERRED EMBODIMENTS

Figure 1:
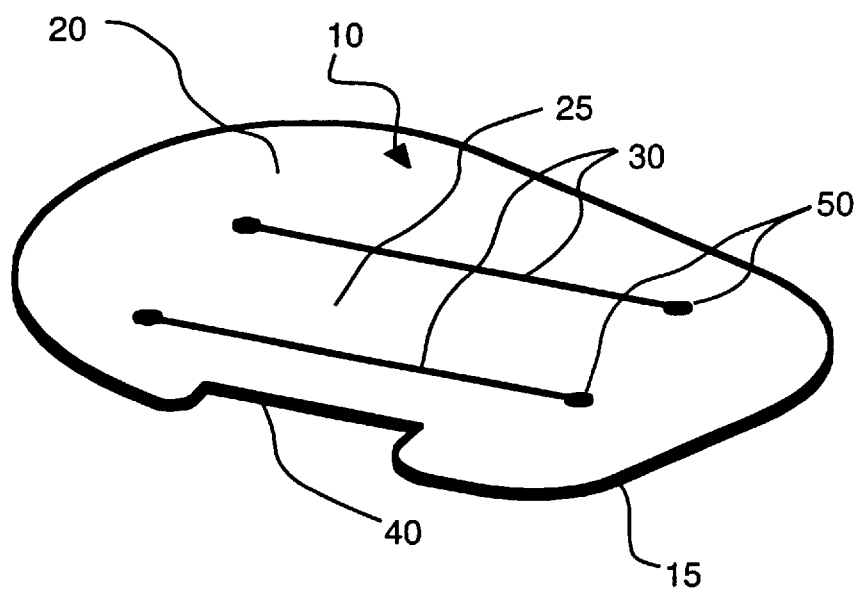
FIG. 1 is a side view of the tongue deflector prior to use according to the teachings of the invention.
Figure 2:
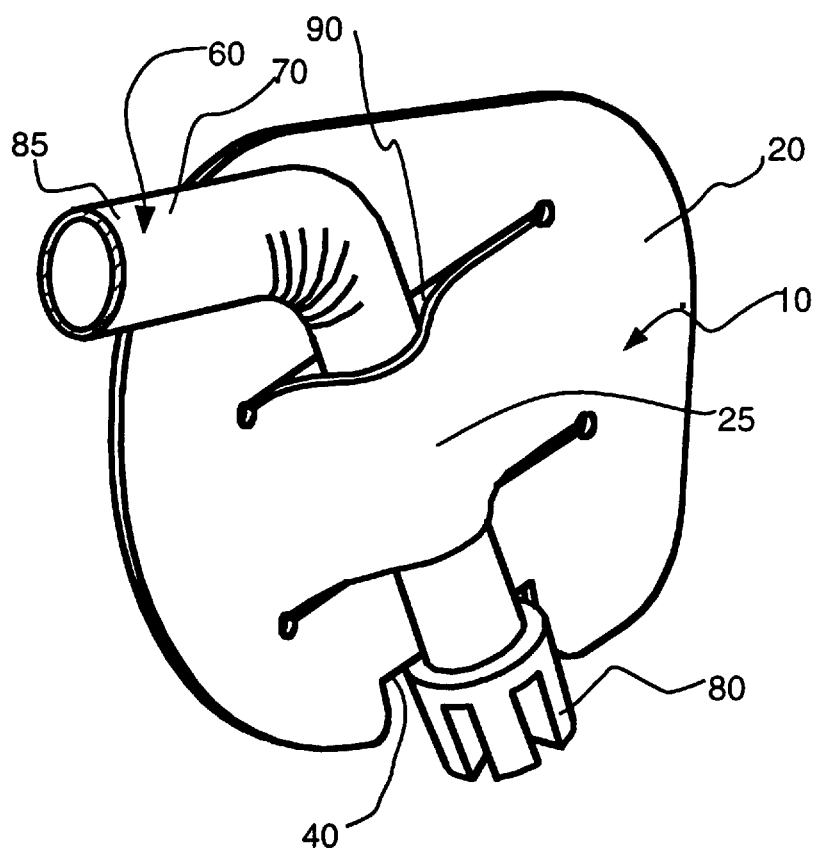
FIG. 2 is a prospective view of the tongue deflector prior to use.
Figure 3:
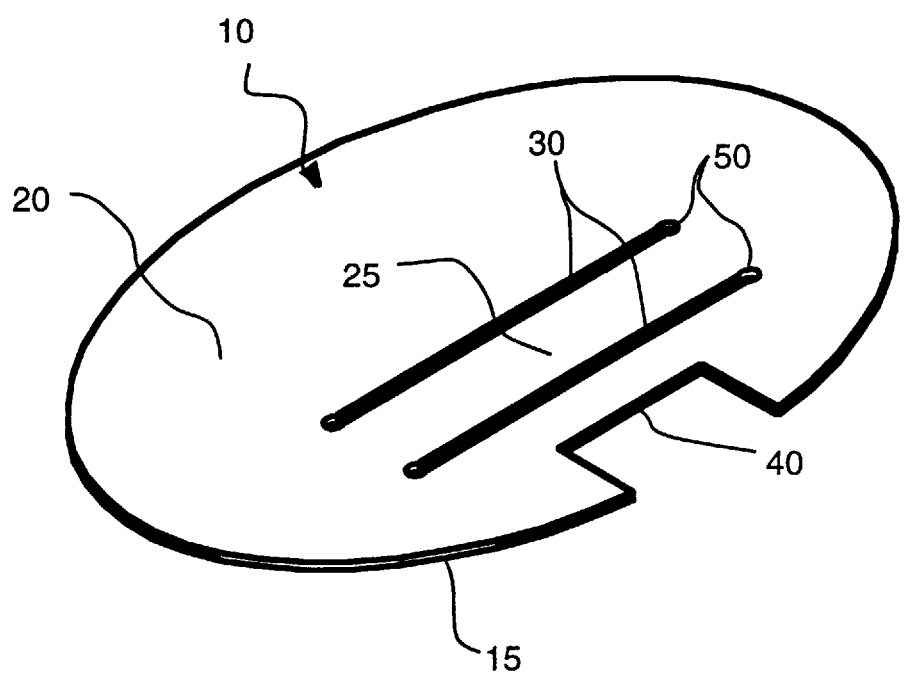
FIG. 3 is a prospective view of the tongue deflector with the saliva ejector tube inserted and the saliva ejector tip positioned in the its designated cutout.
Figure 4:
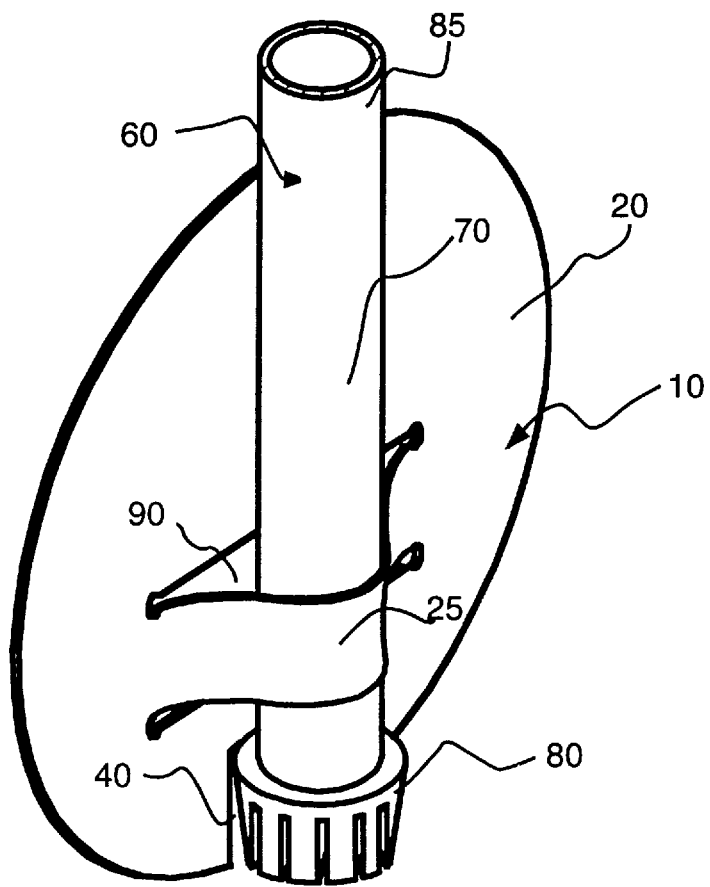
FIG. 4 is a prospective view of the tongue deflector and saliva ejector in the mouth.

Referring now to FIGS. 1 to 6 it is shown therein the numeral 10 designates the tongue deflector, including a flattened body 20 of any conventional flexible material which will not abrade oral tissues, yet substantially rigid to deflect the tongue. Body 20 is of sufficient height to extend from the floor of the mouth to the teeth, so that the body may extend along the inner sides of the teeth to block contact between the tongue and at least some of the teeth. A plurality of cuts 30 are provided through the body 20, preferably longer then the diameter of the saliva ejector stem and preferably of sufficient width to easily separate from body 20. Cuts 30 are spaced apart in substantial parallel alignment from each other and are angled such that the saliva ejector tip 80 is directed towards the rear of the mouth. Cuts 30 form strap 25 in body 20, which are separated from body 20 at two ends. Cuts 30 are preferably terminated with holes 50 of greater diameter then the width of the cuts. Preferably, body cutout 40 is provided in body 20, and is preferable larger than the diameter of the saliva ejector tip 80.

Preferably cut 30 is made to form a slotted groove, further simplifying the separation of the strap 25 from body 20, where termination holes 50 are of greater diameter then the width of the slotted grooves. In addition, multiple straps can be made in body 20 to further enhance the attachment and stability of the tongue deflector to the saliva ejector stem.

In operation, strap 25 is pulled or pushed away from the body 20 providing separation 90 between the strap 25 and body 20. The suction inlet end 85 of saliva ejector 60 is then inserted into separation 90 and the saliva ejector stem 70 is pushed between strap 25 and body 20. Saliva ejector stem 70 is pulled through separation 90 until saliva ejector tip 80 nests in the saliva ejector cutout 40.

Preferably body 10 is made of soft pliable and flexible material which can be easily flexed to extend strap 25, yet sufficiently rigid to provide the required mouth support and strength to withstand dental instruments; still soft enough to be easily trimmed and modified with scissors or sharp instruments to alter size or shape. It is also preferred that slotted cuts 30 be terminated with holes 50 to provide stress relief at the strap-body interface. It is also preferred that body 10 include cutout 40 for accommodating saliva ejector tip 80. It is also preferred that edges 15 of body 10 form a curved surface to reduce the exposure the soft tissue to sharp surfaces. It is also preferred that slotted cuts 30 be at an angle to form strap 25 which orients the inserted saliva ejector tip 80 toward the rear of the mouth, reducing the required bending of stem 70 for saliva ejector 60 to exit the mouth.

Figure 5:
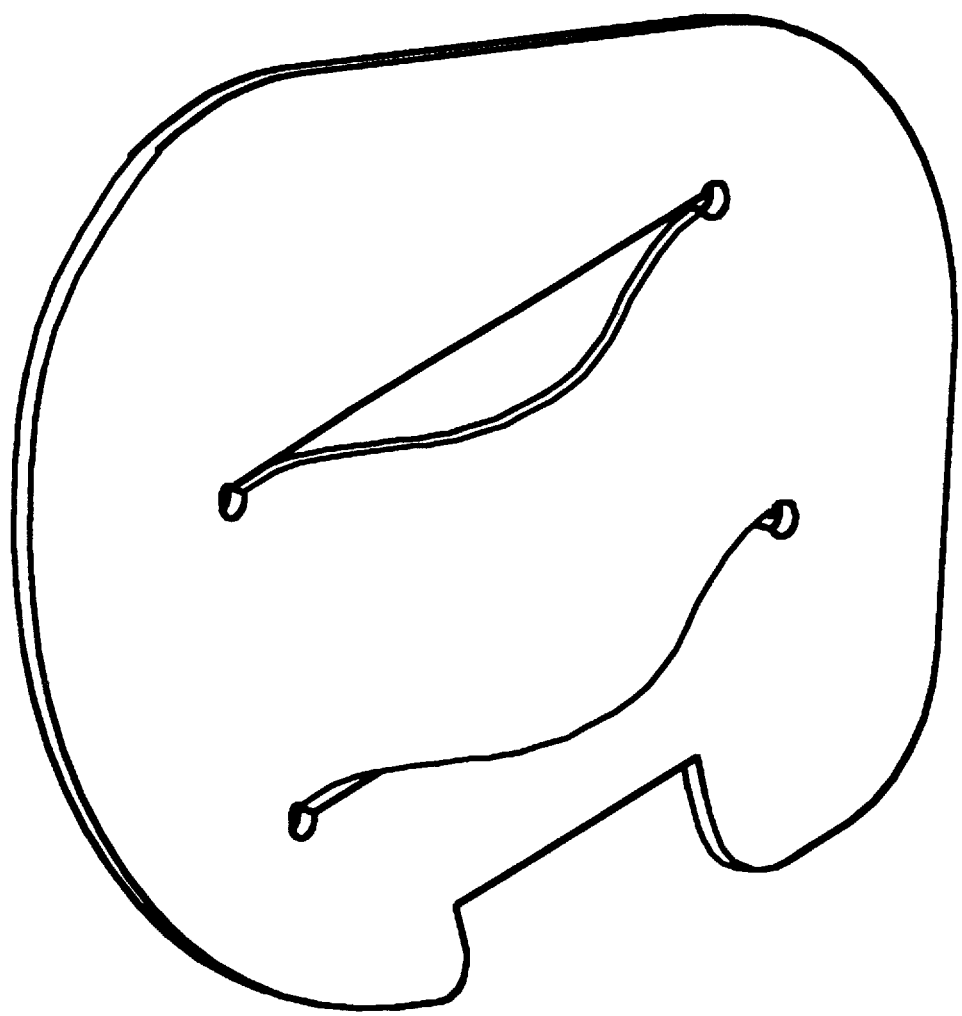
FIG. 5 is a prospective view of the an alternative embodiment of the tongue deflector where the tongue deflector loop is molded into shape.
Figure 6:
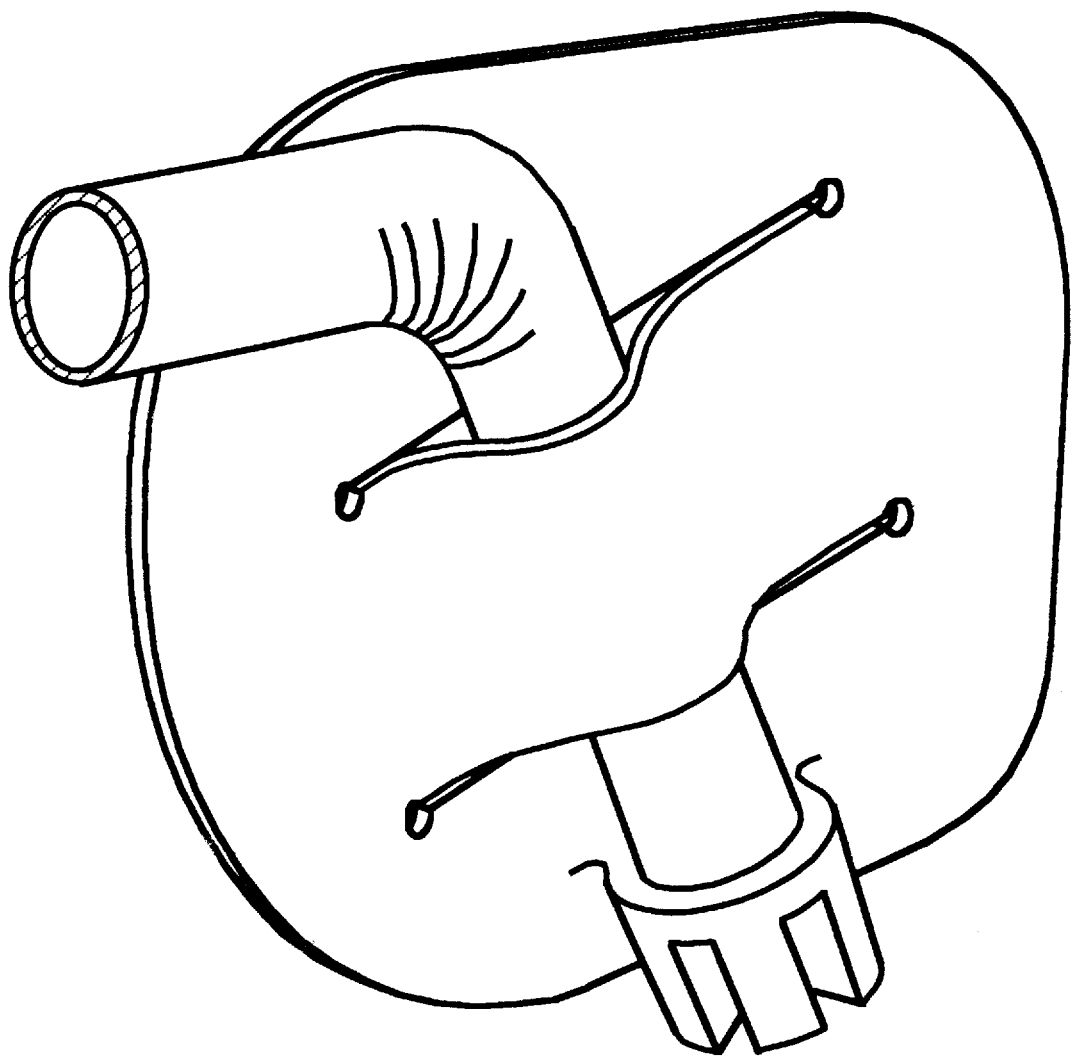
FIG. 6 is a prospective view of another alternative embodiment of the tongue deflector where the tongue deflector is integrated with the saliva ejector tip into a single unit.

It will be apparent to those skilled in the art that various other modifications and variations in addition to those mentioned above could be made to the tongue deflector of this invention without departing from the scope and spirit of the invention. One such variation is shown in FIG. 5, where the tongue deflector is integrally molded of pliable and flexible material, with said strap 25 molded as a curved surface ready to accept saliva ejector stem 70, simplifing the insertion of saliva ejector 60. Another variation of this invention is shown in FIG. 6, where the tongue deflector is integrated with saliva ejector tip 80 as a single unit.

I claim:

1. A protective tongue deflector for use with a saliva ejector comprising:

a flat body of flexible material of sufficient height to extend from the floor of the mouth to the teeth, and;

a plurality of slits extending through the body;

wherein the slits are parallel to one another to form a strap therebetween;

whereby the tongue deflector may be mounted onto a stem of the saliva ejector by pushing or pulling the strap away from the flat body to form a separation between the body and the strap which receives the saliva ejector stem.

2. A protective tongue deflector for use in combination with a saliva ejector as defined in claim 1, wherein a plurality of straps are provided for engaging and attaching to said saliva ejector stem.

3. A protective tongue deflector for use in combination with a saliva ejector as defined in claim 1, wherein a cutout is provided in the body for accommodating a tip of the saliva ejector.

4. A protective tongue deflector for use in combination with a saliva ejector as defined in claim 1, wherein said flattened body has curved edges to provide a smooth surface.

5. A protective tongue deflector for use in combination with a saliva ejector as defined in claim 1, wherein said tongue deflector is equally effective on both the right or left side of the mouth.

6. A protective tongue deflector for use in combination with a saliva ejector as defined in claim 1, wherein said strap is angled such that a tip of the saliva ejector is directed towards the rear of the mouth, whereby the amount of bending of said saliva ejector stem required for said saliva ejector to exit the mouth is reduced.

7. A method for attaching a tongue deflector to a disposable saliva ejector:

wherein the deflector comprises a flat body of flexible material of sufficient height to extend from the floor of the mouth to the teeth and a plurality of slits extending through the body, wherein the slits are parallel to one another to form a strap therebetween;

the method comprising:

pushing or pulling the strap away from the flat body to form a separation between the body and strap;

pushing a stem of the saliva ejector into the separation to attach the body to the saliva ejector.

* * * * *